(12) United States Patent
Satou et al.

(10) Patent No.: US 6,409,899 B1
(45) Date of Patent: Jun. 25, 2002

(54) GAS SENSOR ELEMENT WITH LEAD-PROOF EFFECT

(75) Inventors: Motoaki Satou, Aichi-gun; Yasumichi Hotta, Mie-gun; Namitsugu Fujii, Yokkaichi; Hiromi Sano, Nagoya, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/511,079

(22) Filed: Feb. 23, 2000

(30) Foreign Application Priority Data

Feb. 25, 1999 (JP) ............................. 11-48467
Dec. 7, 1999 (JP) ............................ 11-347682

(51) Int. Cl.⁷ .......................................... G01N 27/407
(52) U.S. Cl. .................... 204/429; 204/426; 204/427; 204/428
(58) Field of Search .................... 204/421–429

(56) References Cited

U.S. PATENT DOCUMENTS 4,021,326 A * 5/1977 Pollner et al.
4,164,462 A * 8/1979 Ichikawa et al.
5,160,598 A * 11/1992 Sawada et al.
5,368,713 A * 11/1994 Friese et al.
5,423,973 A * 6/1995 Friese et al.
5,593,558 A    1/1997 Sugino et al.
5,849,165 A * 12/1998 Kojima et al.

FOREIGN PATENT DOCUMENTS

| JP | 56-53456 | 5/1981 |
| JP | 09-68515 | 3/1997 |
| JP | 09-113480 | 5/1997 |

* cited by examiner

*Primary Examiner*—T. Tung
(74) *Attorney, Agent, or Firm*—Nixon & Vanderhye P.C.

(57) ABSTRACT

A sensor element has a solid electrolyte body holding a reference gas side electrode and a measurement gas side electrode on surfaces thereof. The measurement gas side electrode is covered with a porous protective layer including a component as a lead getter, which reacts with lead contained in measurement gas. Accordingly, lead is removed from measurement gas by the protective layer not to be attached to the measurement gas side electrode. As a result, the sensor element can be used in measurement gas containing lead, without deteriorating responsibility and output thereof.

5 Claims, 5 Drawing Sheets

GAS SENSOR ELEMENT WITH LEAD-PROOF EFFECT

CROSS REFERENCE TO RELATED APPLICATIONS

This application is based upon and claims the benefit of Japanese Patent Applications No. 11-48467 filed on Feb. 25, 1999, and No. 11-347682 filed on Dec. 17, 1999, the contents of which are incorporated herein by reference.

BACKGROUND OF THE INVENTION

1. Field of the Invention

This invention relates to gas sensor elements constituting various sensors such as oxygen sensors, NOx sensors, HC sensors, or CO sensors, which are used in an exhaust system of an automotive internal combustion engine while being exposed to exhaust gas including lead to control combustion of the internal combustion engine, and a method of producing the same.

2. Description of the Related Art

Figure 7:
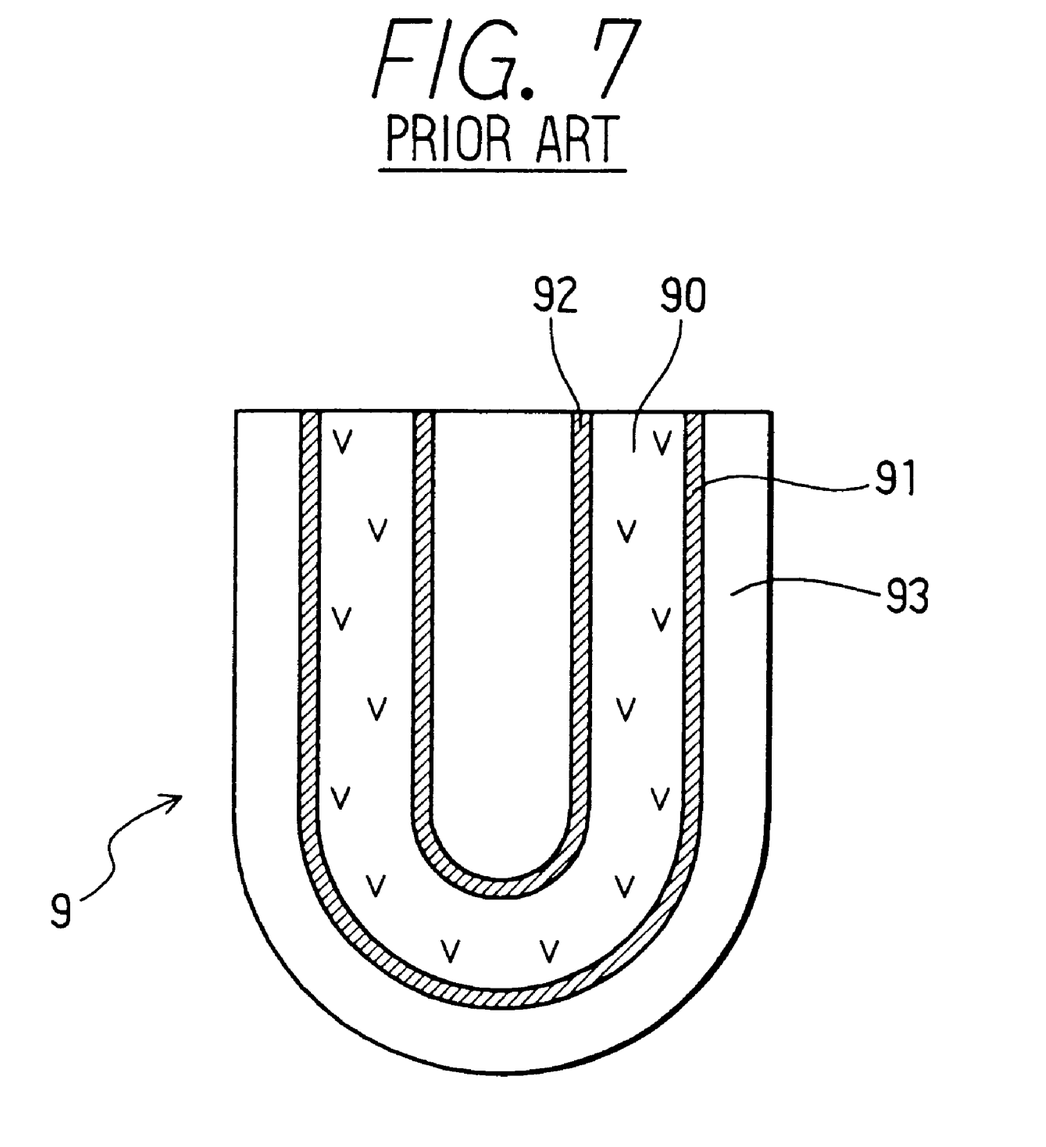
FIG. 7 is a cross-sectional view showing a main portion of a λ sensor element according to a prior art.

A λ sensor element is conventionally used as such an oxygen sensor element for an oxygen sensor, which is disposed in an exhaust gas system of an automotive combustion engine to perform an air fuel ratio feedback control. As shown in FIG. 7, such λ sensor element 9 has a solid electrolyte body 90 having oxygen ion conductivity, a reference gas side electrode 92, and a measurement gas side electrode 91. The reference gas side electrode 92 is provided to be exposed to atmosphere serving as reference gas, and the measurement gas side electrode 91 is provided to be exposed to exhaust gas as measurement gas.

The sensor element 9 further has a porous protective layer 93 formed by plasma spraying and covering the surface of the measurement gas side electrode 92. The porous protective layer 93 restricts a diffusion amount of exhaust gas appropriately to stabilize sensor output, and protects the measurement gas side electrode 91 from being physically and chemically corroded by exhaust gas. The porous protective layer 93 is, however, readily clogged with foreign matters contained in exhaust gas, thereby preventing diffusion of exhaust gas from the porous protective layer 93 excessively. As a result, responsibility and output of the gas sensor element may be lessened.

JP-A-8-50114 and JP-A-9-68515 propose countermeasures against the clogging of the porous protective layer. These countermeasure are effective to the clogging of the protective film by foreign matters such as components added to oil, which are diffused at a solid phase or a liquid phase. However, when exhaust gas includes lead, the conventional countermeasures are non-effective to lead, which is diffused at a gaseous phase. Lead having passed through the protective layer is adhered to the measurement gas side electrode and readily deteriorates sensor characteristics.

JP-A-9-113480 proposes a protective layer including a lead trap layer therein to prevent diffusion of lead to the measurement gas side electrode. However, the lead trap layer includes catalytic metal such as Pt, which also has a catalytic effect to exhaust gas. The lead trap layer absorbs exhaust gas components such as $O_2$, HC, and CO for a long time period by the catalytic effect of the catalytic metal, thereby increasing time required for exhaust gas to pass through the protective layer and retarding exhaust gas from reaching the measurement gas side electrode. As a result, the responsibility of the gas sensor element is decreased.

Further, especially when the protective layer is exposed to lead containing exhaust gas having a temperature higher than 800° C., the catalytic metal traps lead. The catalytic metal having trapped lead becomes to not absorb $O_2$, but to absorbs only unburned components such as HC and CO. Accordingly, the unburned components spend a long time for passing through the protective layer as compared to that of $O_2$. Consequently, sensor output becomes unstable by being decreased only at a rich-gas side. This problem is not peculiar to the oxygen sensor, and occurs in $NO_x$ sensors, CO sensors, HC sensors, and the like similarly.

SUMMARY OF THE INVENTION

The present invention has been made in view of the above problems. An object of the present invention is to provide a gas sensor element usable in measurement gas including lead, without decreasing output and responsibility thereof, regardless of temperature of measurement gas.

According to the present invention, briefly, a gas sensor element has a porous protective layer covering a measurement gas side electrode. The porous protective layer includes a component as a lead getter, which reacts with lead contained in measurement gas. Accordingly, the protective layer can remove lead from measurement gas as a result of reaction between the lead getter and lead.

The measurement gas side electrode is not deteriorated by lead attached thereto. Since the lead getter does not have an absorbing property with respect to measurement gas, measurement gas can pass through the protective layer quickly. Therefore, the sensor responsibility and sensor output are not decreased regardless of temperature of measurement gas.

Preferably, the component as the lead getter in the protective layer reacts with lead at a temperature higher than approximately 500° C. Accordingly, the protective layer can trap lead securely by reacting with lead, which is diffused at a gaseous phase. When the temperature of measurement gas is lower than 500° C., lead is hardly diffused. Therefore, the measurement gas side electrode is not deteriorated by lead. More preferably, the lead getter can react with lead at a temperature up to approximately 1000° C. This is because the temperature of measurement gas may be raised to 1000° C.

Preferably, the lead getter is included in the protective layer as particles having an average particle diameter in a range of approximately 0.2 μm to 2 μm. When the average particle diameter is smaller than 0.2 μm, the protective layer may have cracks therein when it is formed. When the average particle diameter is larger than 2 μm, a surface area of the lead getter is decreased as a whole, resulting in low reactivity with lead. In this case, lead cannot be trapped by the lead getter securely.

Preferably, the lead getter is made of material selected from a group consisting of $WO_3$, $MoO_3$, $La_2O_3$, $FE_2O_3$, $Nb_2O_5$, which can readily react with lead an hardly have an absorbing property to measurement gas. Accordingly, the protective layer can trap lead securely while allowing measurement gas to pass through without delay. Consequently, the sensor outputand sensor responsibility are not decreased.

The protective layer can be formed on the measurement gas side electrode by spraying, dipping, or coating a source material including the component as the lead getter on the measurement gas side electrode. The source material may include metallic oxide particles in addition to lead getter particles. According to this method, a large amount of lead getter particles can be dispersed in the protective layer uniformly.

BRIEF DESCRIPTION OF THE DRAWINGS

Other objects and features of the present invention will become more readily apparent from a better understanding of the preferred embodiments described below with reference to the following drawings, in which.

DETAILED DESCRIPTION OF THE PREFERRED EMBODIMENTS (First Embodiment)

A gas sensor element in a first preferred embodiment is explained with reference to FIGS. 1 to 5 below. The gas sensor element in the first embodiment is a λ sensor element 1, which is a kind of oxygen sensor element. The λ sensor element 1 is used for a λ sensor 2, which is disposed in an exhaust pipe of an automotive engine exhaust system for an air fuel ratio feedback control system.

Figure 1:
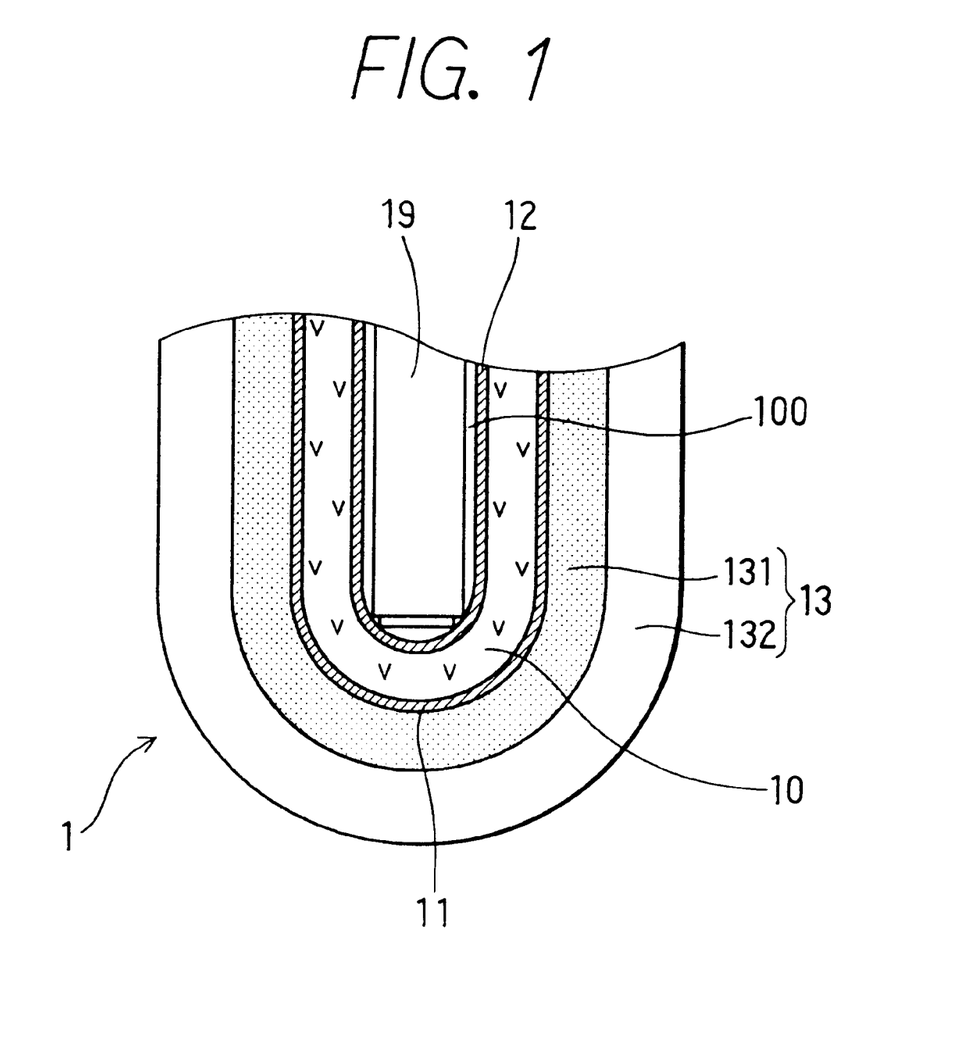
FIG. 1 is a cross-sectional view shoring a main portion of a λ sensor element in a first preferred embodiment.

As shown in FIG. 1, the λ sensor element 1 has a cup-type solid electrolyte body 10 having oxygen ion conductivity and defining an air chamber 100 therein, into which atmosphere is introduced as reference gas, a reference gas side electrode 12 provided to face the air chamber 100, and a measurement gas side electrode 11 provided to face a measurement gas chamber 240 via a porous protective layer 13. A pole heater 19 is disposed in the air chamber 100.

Figure 3:
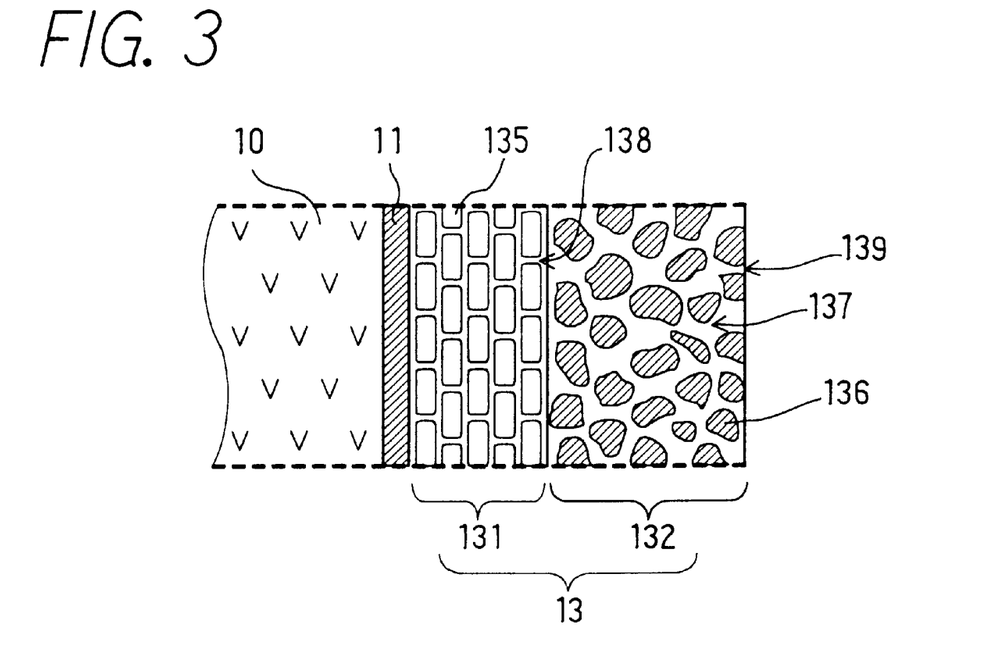
FIG. 3 is a cross-sectional view schematically partially showing a protective layer in the first embodiment.

The protective layer 13 has a two-layer structure composed of a first protective layer 13 contacting the measurement gas side electrode 11 and a second protective layer 132 covering the first protective layer 131. The second protective layer 132 contains lead getters made of $WO_3$. As shown in FIG. 3, the first protective layer 131 includes particles 135 made of heat resistant metallic oxide, and pores 138 defined among the particles 135. The second protective layer 132 includes lead getters 136, and pores 137 defined among the lead getters 136. Reference numeral 139 denotes the surface of the second protective layer 132.

Measurement gas enters the second protective layer 132 from the surface 139, passes through the pores 137 of the second protective layer 132 and the pores 138 of the first protective layer 131, and then reaches the measurement gas side electrode 11. Lead contained in measurement gas reacts with the lead getters 136 while passing through the second protective layer 132, and accordingly is taken into the lead getters 136 as a compound.

Figure 2:
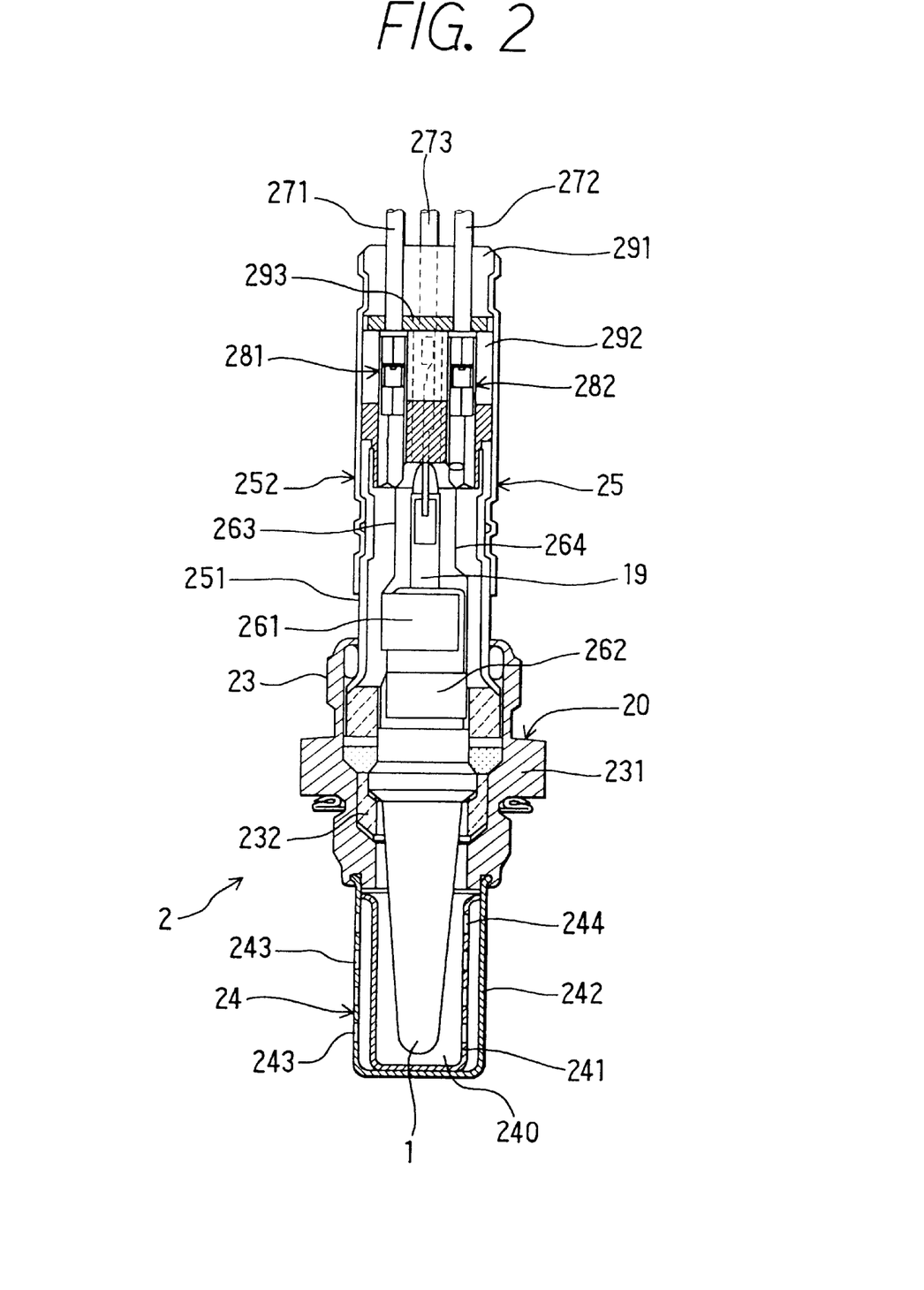
FIG. 2 is a cross-sectional view showing the λ sensor element in the first embodiment.

Next, the λ sensor 2 holding the λ sensor element 1 is explained. As shown in FIG. 2, the λ sensor 2 is composed of the λ sensor element 1 and a housing 20 for fixedly holding the λ sensor element 1 inserted therein. The housing 20 has a core portion 23 formed with a flange 231 generally at a central portion thereof, a measurement gas side cover 24 at a lower side of the core portion 23, and an atmosphere side cover 25 at an upper side of the core portion 23. The measurement gas side cover 24 is inserted into the exhaust pipe, and the atmosphere side cover 25 is exposed to atmosphere.

The measurement gas side cover 24 is composed of an inside cover 241 and an outside cover 242, which are made of stainless and are formed with conduction holes 243, 244, respectively, for conducting measurement gas into the measurement gas chamber 240 defined inside the inside cover 241. The atmosphere side cover 251 is composed of a main cover 21 attached to the core portion 23, and a subordinate cover 252 covering a rear end portion of the main cover 251. The main cover 251 and the subordinate cover 252 respectively have atmosphere conduction holes not shown.

The λ sensor element 1 is held inside the core portion 23 via an insulation member 232. Metallic plate terminals 261, 262 are connected to the reference gas side electrode 12 and the measurement gas side electrode 11 of the λ sensor element 1. Further, band like terminal pieces 263, 264 are connected to the plate terminals 261, 262 at an end side thereof, and are connected to connectors 281, 282 at the other end side thereof. The connectors 281, 282 are connected to lead wires 271, 272.

The plate terminals 261, 262 are formed by deforming inversely T-shaped metallic plates into cylinders, and contact either of the reference side electrode 12 and the measurement gas side electrode 11. Appropriate contact pressures are imparted by spring elastic strengths of the metallic plates, between the plate terminals 261, 262, and the reference gas side electrode 12 and the measurement gas side electrode 11.

On the other hand, a tensile force is applied to the lead wires 271, 272 in an axial direction of the λ sensor 2 so that the plate terminals 261, 262 are drawn through the connectors 281,282. The plate terminals 261, 262 can be shifted in the axial direction accordingly. Therefore, a stopper 293 is provided between rubber bushes 291, 292 at an end portion of the λ sensor 2. The stopper 293 is provided to prevent the shift of the connectors 281, 282, and is made of resin to keep an insulating property between the lead wires 271, 272. Reference numeral 273 denotes a lead wire for supplying electricity to the heater 19. The λ sensor 2 is attached to the exhaust system by inserting the exhaust cover 24 into the exhaust pipe, and by fixing the flange 231 inside the exhaust pipe.

Next, a method of producing the λ sensor element 1 is explained below. First, $ZrO_2$ mixed with 5 mol % $Y_2O_3$ is ground and then granulated by a spray dryer, thereby forming powdery material. The solid electrolyte body 10 is provided by forming the powdery material into a specific shape and baking it at 1600° C. for 2 hours. The surface of the solid electrolyte body 10 is roughened by strong acid. After that, the measurement gas side electrode 11 and the reference gas side electrode 12 are formed on the solid electrolyte body 10 by chemical plating.

The porous first protective layer 131 is formed on the measurement gas side electrode 11 from heat resistant metallic oxide such as $MgO.Al_2O_3$ spinel by plasma spraying. Next, lead getters 136 made of $WO_3$ is mixed with water, and an inorganic binder is added at 0.5 to 10 wt % with respect to a solid component, thereby forming slurry. The slurry is coated on the first protective layer 131 by dipping or spraying. Then, the slurry is dried and is baked at 500 to 1000° C. The second protective layer 132 including the lead getters 136 shown in FIG. 3 is formed accordingly. As a result, the λ sensor element 1 in the present embodiment is provided.

The second protective layer 132 may be formed from slurry including the lead getters 136, heat resistant metallic oxide such as $\gamma$-$Al_2O_3$, $\alpha$-$Al_2O_3$, or $MgO.Al_2O_3$ spinel, and water to include the lead getters 136 and heat resistant metallic oxide powders.

Next, characteristics of the $\lambda$ sensor element 1 in the present embodiment were evaluated using samples 1 to 24 indicated in Table 1.

TABLE 1

| SAMPLE | LEAD GETTER | PARTICLE DIAMETER ($\mu$m) | WEIGHT (mg) | LEAD-PROOF EFFECT 650° C. | LEAD-PROOF EFFECT 850° C. |
|---|---|---|---|---|---|
| 1 | $WO_3$ | 0.2 | 5 | Δ | Δ |
| 2 | ↑ | ↑ | 10 | ○ | ○ |
| 3 | ↑ | ↑ | 30 | ⊙ | ⊙ |
| 4 | ↑ | ↑ | 60 | ⊙ | ⊙ |
| 5 | ↑ | ↑ | 100 | ⊙ | ⊙ |
| 6 | ↑ | 1 | 300 | ⊙ | ⊙ |
| 7 | ↑ | 0.1 | ↑ | ⊙ | ⊙ |
| 8 | ↑ | 1.0 | ↑ | ⊙ | ⊙ |
| 9 | ↑ | 2.0 | ↑ | ○ | ○ |
| 10 | ↑ | 10 | ↑ | Δ | Δ |
| 11 | ↑ | 20 | ↑ | Δ | Δ |
| 12 | $\gamma$-$Al_2O_3$ + $WO_3$ | 0.2 | 5 | Δ | Δ |
| 13 | ↑ | ↑ | 10 | ○ | ○ |
| 14 | ↑ | ↑ | 30 | ⊙ | ⊙ |
| 15 | ↑ | ↑ | 60 | ⊙ | ⊙ |
| 16 | ↑ | ↑ | 100 | ⊙ | ⊙ |
| 17 | ↑ | 1 | 300 | ⊙ | ⊙ |
| 18 | ↑ | 0.1 | ↑ | ⊙ | ⊙ |
| 19 | ↑ | 1.0 | ↑ | ⊙ | ⊙ |
| 20 | ↑ | 2.0 | ↑ | ○ | ○ |
| 21 | ↑ | 10 | ↑ | Δ | Δ |
| 22 | ↑ | 20 | ↑ | Δ | Δ |
| 23 | NO | — | — | X | X |
| 24 | $\gamma$-$Al_2O_3$ + Pt | — | — | Δ | X |

Samples 1 to 11 have second protective layers including only $WO_3$ for lead getters having various average particle diameters and various weights. Samples 12 to 22 have second protective layers each including $WO_3$ as lead getters and $Al_2O_3$, and having a thickness of 200 $\mu$m. In each sample, the first protective layer is formed from MgO—$Al_2O_3$ spinel by plasma spraying to have a thickness of 100 $\mu$m. Table 1 shows the average particle diameters of the lead getters and the weights of $WO_3$ contained in the respective second protective layers in samples.

Sample 23 is a $\lambda$ sensor element having two protective layers composed of only $\gamma$-$Al_2O_3$ and not including $WO_3$. Sample 24 has a protective layer composed of MgO—$Al_2O_3$ covered with a layer, which includes $\gamma$-$Al_2O_3$ particles holding Pt as catalyst 15 and has a thickness of 200 $\mu$m. The content of Pt with respect to the amount of MgO—$Al_2O_3$ is approximately 2mol %.

The lead-proof effect of $\lambda$ sensor elements of samples 1 to 24 were evaluated in the following manner. Specifically, each $\lambda$ sensor element was disposed in an exhaust system of an automotive engine, which uses gasoline fuel containing lead at 0.4 g/l, and the engine was started. Then, an acceleration endurance test was performed when exhaust gas temperature was 650° C. and 850° C.

Figure 4:
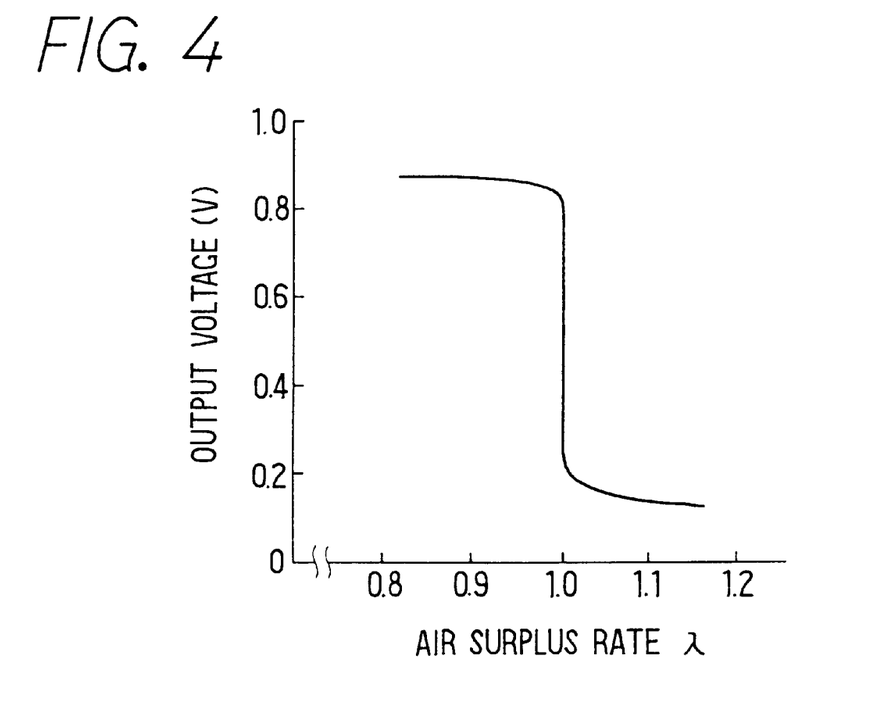
FIG. 4 is a graph showing a relationship between an air surplus rate and an output voltage of each sample before an endurance test in the first embodiment.

A relationship between an air surplus rate $\lambda$ and an output voltage V of each $\lambda$ sensor element of samples 1 to 24 was measured before performing the acceleration endurance test. As shown in FIG. 4, in every $\lambda$ sensor element, the output voltage V suddenly changed at around $\lambda$=1 to have a waveform having a large difference in output voltage between a rich side and a lean side. This is because combustion reaction of components such as HC and CO contained in exhaust gas rapidly progresses by oxygen due to the catalytic effect of the measurement gas side electrode. The $\lambda$ sensor element gradually deteriorates by the acceleration endurance test, so that the difference in output voltage between the rich side and the lean side decreases.

In the present embodiment, the difference in output voltage was measured when the air surplus rate $\lambda$ was 0.9 and was 1.1 in each sample. Then, the time period for decreasing the difference in output voltage to 0.5 or less was used to evaluate the lead-proof effect shown in Table 1. Specifically, each sample was determined as "x" when the time period of the $\lambda$ sensor element was in a range of 100 to 200 hours, as "Δ" when the time period was in a range of 200 to 400 hours, as "○" when the time period was in a range of 400 to 800 hours, or as "⊙" when the time period was 800 hours or more.

As known from Table 1, the $\lambda$ sensor elements of samples 1 to 22 having the second protective layers including the lead getters are superior to those of samples 23, 24, which do not have the protective layers including the lead getters. It is further confirmed that samples 2 to 9, and 13 to 20 including $WO_3$, average particle diameters of which are in a range of 0.1 $\mu$m to 2 $\mu$m and weights of which are larger than 5 mg, have especially superior lead-proof effects.

This is because $WO_3$ reacts with lead to form a lead compound. Accordingly, lead is trapped by $WO_3$ not to reach the measurement gas side electrode, so that the catalytic effect by the measurement gas side electrode is not prevented by lead. As a result, the combustion reaction of the components such as HC and CO in exhaust gas and oxygen can rapidly progress by the measurement gas side electrode. The output voltage can have a stable waveform for a long time period.

Figure 5:
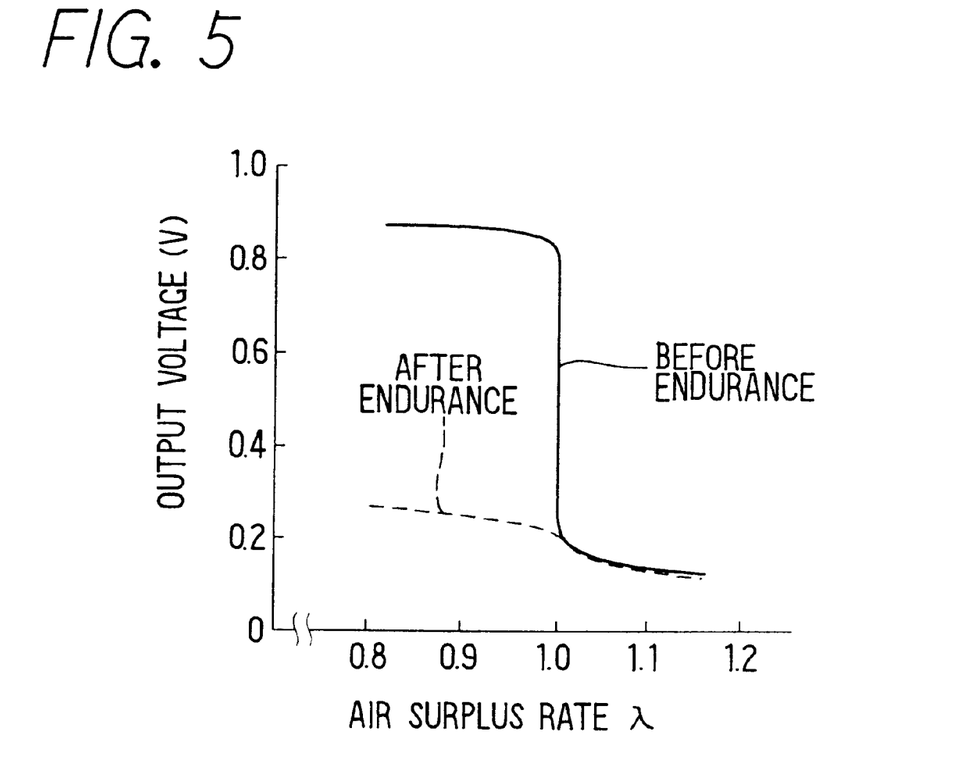
FIG. 5 is a graph showing a relationship between an air surplus rate and an output voltage of sample 23 before and after the endurance test in the first embodiment.

It is further confirmed that the $\lambda$ sensor element of sample 23, which has not protective layer including the lead getters, hardly exhibits the lead-proof effect. Specifically, because the $\lambda$ sensor element does not have the protective layer for trapping lead, the measurement gas side electrode is easily covered with lead in a short time period not ot absorb oxygen thereon. That is, the catalytic effect of the measurement gas side electrode deteriorates, and accordingly, it becomes hard for the components such as HC and CO in exhaust gas and oxygen to progress the combustion reaction. The relationship between the air surplus rate λ and the output voltage of sample 23 is shown in FIG. 5. As shown in the figure, the difference in output voltage becomes very small by undergoing the acceleration endurance test.

It is further confirmed that the λ sensor element of sample 24 is not endurable in practical usage especially when the temperature of exhaust gas is high, because the difference in output voltage is decreased. This is because Pt trapping lead in exhaust gas at high temperature of 800° C. or more selectively absorbs unburned components such as HC and Co in exhaust gas without absorbing $O_2$. Accordingly, the time required for the unburned components to pass through the protective layer is increased as compared to that of $O_2$, and the output voltage at the rich side is lessened.

On the other hand, in samples 1, 12 in which the weights of $WO_3$ are smaller than 5 mg, the lead-proof effects were slightly small as compared to those of other samples. In samples 10, 11, 21, 22 in which the average particle diameters of $WO_3$ are 10 $\mu$m or more, likewise, the lead-proof effects were slightly small as compared to those of other samples. This is because reactivity to lead is small in such samples.

It is further confirmed that samples 13 to 20, in each of which the second protective layer composed of $WO_3$ and $Al_2O_3$ having an average particle diameter of 20 $\mu$m is formed on the first protective layer, have sufficient lead-proof effects and sufficient clogging-proof effects simultaneously. This is because the irregularity of the surface of the second protective layer is large, and therefore a film not having air permeability cannot be continuously formed on the surface of the λ sensor element by deposition of oil components and the like such as P, Zn, Ca, Si, and K contained in exhaust gas. Accordingly, fine pores are secured on the surface of the protective layer to provide a flow path for measurement gas.

The effects according to the present embodiment are summarized below. The λ sensor element in the present embodiment has the second protective layer including the lead getters made of $WO_3$. The lead getters react with lead contained in measurement gas to remove lead from measurement gas. Accordingly, the measurement gas side electrode is prevented from being deteriorated by lead attached thereto. Even when the λ sensor element is exposed to measurement gas containing lead with high temperature, the lead getters, which is not made of catalytic metal, does not have an absorbent property to measurement gas, and allow measurement gas to pass through the protective layer. Accordingly, deterioration in responsibility and decreased output of the λ sensor element can be prevented.

Further, as shown in FIG. 3, the lead getters 136 is contained in the second protective layer 132 as particles. The reaction of the lead getters 136 with lead to form a compound increases diameters of the lead getters 136 just slightly. Therefore, the pores 137 defined in the protective layer 132 are hardly clogged by the increase in diameter of the lead getters 136, when an initial porosity and pore diameters of the protective layer 132 are set by estimating the increase in diameter of the lead getters 136. When the clogging of the pores 137 do not occur, measurement gas can pass through the protective layer 132 without delay.

Further, clogging of the pores 138 of the first protective layer 131 by the lead getters 136 invaded thereinto can be prevented by appropriately controlling the particle diameter of the lead getters 136. Accordingly, measurement gas is not interrupted from passing through the first and second protective layers 131, 132, and the responsibility is not lowered.

Thus, according to the present embodiment, the λ sensor element is usable in measurement gas containing lead with responsibility and output voltage, which are hardly decreased regardless of temperature. The λ sensor element in the present embodiment is used for the λ sensor, which is used for the air fuel ratio feedback control system of the automotive engine. In this case, the λ sensor element in the present embodiment can provide a stable air fuel ratio feedback control with respect to the automotive engine using gasoline containing lead, because the responsibility and the output of the λ sensor element are not decreased largely as described above. Accordingly, a three-way catalytic converter, which is disposed in the exhaust system of the engine, can be maintained at a good condition, resulting in high purification efficiency to exhaust gas.

(Second Embodiment)

Figure 6:
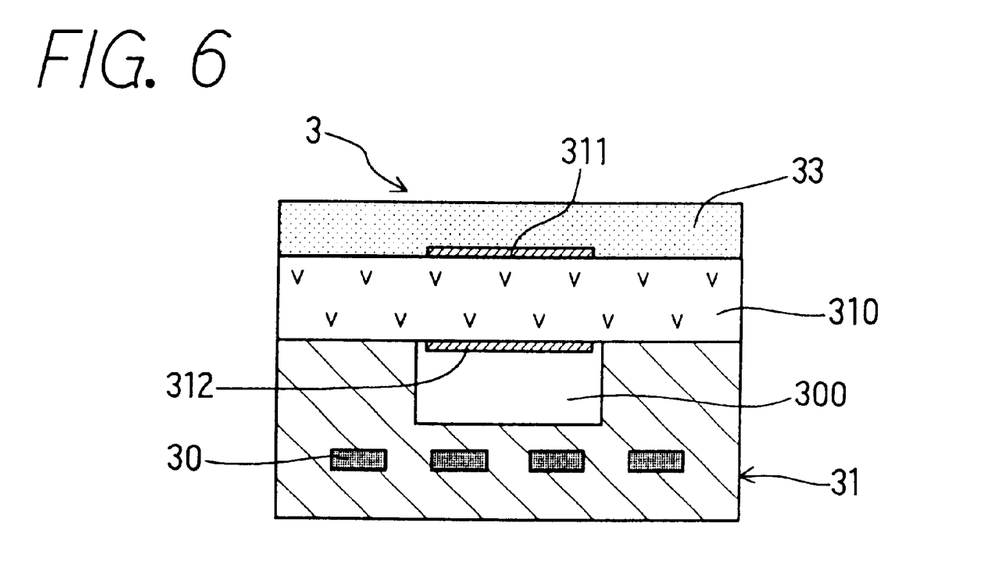
FIG. 6 is a cross-sectional view showing a main portion of a lamination type λ sensor element in a second preferred embodiment.

As shown in FIG. 6, a λ sensor element 3 in a second preferred embodiment is a lamination type sensor element integrally having a heater 31. The λ sensor element 3 has a plate solid electrolyte body 310 and the heater 31 integrated with the solid electrolyte body 310 to defined an air chamber 300 for introducing atmosphere. Heat generating members 30 are buried in the heater 31. A measurement gas side electrode 311 and a reference gas side electrode 312 are provided on the surfaces of the solid electrolyte body 310. A protective layer 33 including lead getters made of $WO_3$ is provided on the surface of the measurement gas side electrode 311. The other features are the same as those in the first embodiment. The lamination type λ sensor element in the second embodiment can provide the same effects as those of the cup type λ sensor element in the first embodiment.

In the first and second embodiments, the present invention is applied to the λ sensor elements used for the λ sensors, but is not limited to those. The present invention is available for other sensors such as lean sensors, which are critical current type oxygen sensors, A/F sensors, $NO_x$ sensors, CO sensors, and HC sensors.

While the present invention has been shown and described with reference to the foregoing preferred embodiment, it will be apparent to those skilled in the art that changes in form and detail may be made therein without departing from the scope of the invention as defined in the appended claims.

What is claimed is:

1. A gas sensor element comprising:
   a solid electrolyte body;
   a reference gas side electrode disposed on a first surface of the solid electrolyte body to contact a reference gas;
   a measurement gas side electrode disposed on a second surface of a solid electrolyte body to contact a measurement gas; and
   a porous protective layer covering a surface of the measurement gas side electrode and including a component which reacts with lead contained in the measurement gas;

wherein the component is selected from a group consisting of $WO_3$, $MoO_3$, $Fe_2O_3$, and $Nb_2O_5$.

2. The gas sensor element of claim 1 wherein:

the protective layer has first and second protective layers; and the component is included in one of the first and second protective layers.

3. The gas sensor element of claim 1, wherein the component reacts with the lead at a temperature higher than approximately 500° C.

4. The gas sensor element of claim 1, wherein the component is contained in a protective layer as particles having an average particle diameter in a range of approximately 0.2 $\mu$m to 2 $\mu$m.

5. The gas sensor element of claim 4, wherein the protective layer includes a first group of particles made of the component which reacts with the lead and having a first average particle diameter in a range of approximately 0.2 $\mu$m to 2 $\mu$m, and a second group of particles made of a material different from the component.

* * * * *